United States Patent
Sakamoto et al.

[11] Patent Number: 6,073,493
[45] Date of Patent: Jun. 13, 2000

[54] METHOD OF DIAGNOSING FATIGUE LIFE OF STRUCTURAL STEELWORK AND A MEMBER OF STEELWORK HAVING LIFE DIAGNOSTIC FUNCTION

[75] Inventors: Hiroaki Sakamoto; Toru Inaguma, both of Kawasaki; Yasuhiro Nakata; Mitsuhiko Yazaki, both of Tokyo, all of Japan

[73] Assignee: Nippon Steel Corporation, Tokyo, Japan

[21] Appl. No.: 09/002,909

[22] Filed: Jan. 5, 1998

[30] Foreign Application Priority Data

Jan. 10, 1997 [JP] Japan .................................. 9-014568

[51] Int. Cl.[7] .................................................. G01N 29/04
[52] U.S. Cl. ............................... 73/801; 324/209; 73/779
[58] Field of Search ..................... 73/779, 801; 324/209, 324/237, 238, 240

[56] References Cited

U.S. PATENT DOCUMENTS

| | | | |
|---|---|---|---|
| 4,599,563 | 7/1986 | Titto et al. | 73/779 |
| 4,689,558 | 8/1987 | Ruushanen et al. | 73/801 |
| 4,931,730 | 6/1990 | Olsen et al. | 73/779 |
| 5,166,613 | 11/1992 | Perry | 73/779 |
| 5,619,135 | 4/1997 | Kohn et al. | 73/779 |

FOREIGN PATENT DOCUMENTS

| | | |
|---|---|---|
| 59-135362 | 8/1984 | Japan . |
| 60-257354 | 12/1985 | Japan . |
| 61-172059 | 8/1986 | Japan . |
| 61-161659 | 10/1986 | Japan . |
| 1-269049 | 10/1989 | Japan . |
| 4-125463 | 4/1992 | Japan . |
| 7-174730 | 7/1995 | Japan . |

*Primary Examiner*—Max Noori
*Attorney, Agent, or Firm*—Kenyon & Kenyon

[57] ABSTRACT

In a method of diagnosing the fatigue life of structural steelwork according to the present invention, a Barkhausen noise measurement is performed under the condition of 5 $\mu m \leq d \leq 1$ mm where d is the detection depth of Barkhausen noise, by using a magnetic head constituted by an air-core coil detection head and a magnetic excitation head obtained by winding a copper wire such as an enameled wire on a U-shaped core made of a soft magnetic material such as a silicon steel sheet or an amorphous magnetic material. The degree of fatigue damage of a target measurement portion is diagnosed using the root-mean-square (RMS) voltage or voltage amplitude value of the Barkhausen noise. According to this method, the degree of fatigue and degradation by stress and strain in the structural steelwork can be accurately diagnosed prior to development of cracking without any limitation on diagnostic locations. A member of steelwork having a life diagnostic function is obtained by mounting the above magnetic head on a brace- or wall-like vibration-damping device made of very low-yield steel. According to this member of steelwork, the wall or covering material of a bridge or the like need not be removed even in practicing a fatigue life diagnosis. The degree of fatigue degradation in structural steelwork can be easily and accurately diagnosed prior to development of cracking even in a location where an operator cannot access due to the structural limitation.

20 Claims, 9 Drawing Sheets

METHOD OF DIAGNOSING FATIGUE LIFE OF STRUCTURAL STEELWORK AND A MEMBER OF STEELWORK HAVING LIFE DIAGNOSTIC FUNCTION

BACKGROUND OF THE INVENTION

1. Field of the Invention

The present invention relates to a method of diagnosing the fatigue life of structural framework such as buildings, bridges, and other constructions whose main structures are made of steel, and a member of steelwork having a life diagnostic function.

2. Description of the Related Art

A member of steelwork constituting a building is susceptible to fatigue damage more or less by vibrations caused by the wind or earthquake after it has been built up. The fatigue and damage progress in bridges due to repeated vibrations caused by vehicles passing on them. To prevent destruction resulted from the fatigue damage, the following conventional methods have been practiced: a method of calculating a degree of strain in a structure in advance and estimating the life of the structure; and a method mainly using visual inspection such as a color check if it is assumed that cracking has occurred due to the fatigue and damage. These conventional methods cannot accurately diagnose an actual degree of fatigue damage to determine whether to repair. There has recently been proposed a vibration-damping device having a vibration-damping function, in which low-yield steel is incorporated in structual component with a form of a wall or brace. No technique for accurately diagnosing the degree of fatigue damage and determining whether to repair is developed for the above device.

An attempt has been made to nondestructively inspect the material and stress of a target measurement object by using the fact that the magnetic properties of the material depend on the microstructures, such as the crystal grain size and a precipitate or the like, and strain.

The following examples are disclosed as a method and/or apparatus for nondestructively inspecting the degree of degradation of a material: a method of inspecting the degree of degradation by calculating the ferrite generation amount of a high-temperature gas furnace member from its magnetic susceptibility (Japanese Patent Laid-Open No. 59-135362); an apparatus for diagnosing the degree of material degradation of a steel pipe by eddy current (Japanese Patent Laid-Open No. 60-257354); a method of diagnosing the degree of material degradation of a turbine rotor from its ECT value and hardness to predict the destruction lifetime (Japanese Patent Laid-Open No. 61-172059); an apparatus for detecting the degree of degradation of low-alloy steel from its magnetic permeability (Japanese Utility Model Laid-Open No. 61-161659); a method of measuring changes in magnetic domain wall movement characteristics of a ferromagnetic body over time to inspect the degree of brittlement of the material by comparing the measured changes with a master-curve obtained in advance (Japanese Patent Laid-Open No. 1-269049); and a method of quickly measuring the degree of degradation of a metal material in a radiation environment by using a plurality of magnetic sensors (Japanese Patent Laid-Open No. 4-125463).

The above conventional techniques, however, detect material degradation caused by changes in microstructures such as phase transformation when a target measurement object is set in a high-temperature state or exposed to radiation. These conventional techniques are not directed to detection of fatigue degradation caused by the stress or strain, which is the object of the present invention. In addition, the detection means used in the conventional techniques are the eddy current and magnetic permeability and do not use Barkhausen noise.

The following methods are proposed as a method using Barkhausen noise: a method of estimating the degree of fatigue degradation of mild steel (L. P. Karjalainen et al., IEEE Trans. Mag. MAG-16, 514 (1980)); and a method of estimating the toughness of tool steel (Nakai et al., Iron and Steel, 75,833 (1989)). The result by L. P. Karjalainen in IEEE Trans. Mag. MAG-16, 514 (1980) exhibits a change in Barkhausen noise in a fatigue test in which a magnetic head is brought into tight contact with a thin mild steel piece. More specifically, this reference exhibits an abrupt change in Barkhausen noise prior to the fracture of the test piece. No description, however, is made for Barkhausen noise measurement conditions under which the degree of fatigue can be accurately detected in an actual structure and the life of the actual structure can be diagnosed, provided that the magnetic head cannot be brought into direct contact with a measurement location due to, e.g., an uneven surface or the presence of a covering material.

As described above, the fatigue damage by stress and strain in structural steelwork are conventionally diagnosed by mainly visual inspection. Such a diagnosis is performed upon removing a wall or covering material in a building or the like, resulting in high cost. Visual inspection is also mainly performed for bridges. The visual inspection never detects cracking until it has developed and grown up to some extent. A location where an operator cannot access due to the structural limitation cannot be subjected to the fatigue diagnosis. Neither a method of diagnosing the fatigue life of an actual structure nor a member of steelwork capable of practicing the method is available.

SUMMARY OF THE INVENTION

It is an object of the present invention to provide a method of easily and accurately diagnosing the degree of fatigue degradation by stress and strain in structural steelwork prior to occurrence of cracking without any limitation on diagnostic locations, and a member of steelwork capable of practicing this method.

A method of diagnosing the fatigue life of structural steelwork according to the present invention comprises disposing a magnetic head constituted by a magnetic excitation head and a magnetic detection head so as to be spaced apart above from a target measurement member requiring a fatigue damage diagnosis by a liftoff distance of 5 $\mu$m or more to 4 mm or less, detecting Barkhausen noise with the magnetic detection head under a condition of 5 $\mu$m$\leq$d$\leq$1 mm where d is a detection depth of the Barkhausen noise after a target measurement portion is AC-magnetized with the magnetic excitation head, and diagnosing a degree of fatigue damage of the target measurement portion in accordance with one of a root-mean-square voltage and voltage amplitude value of the Barkhausen noise.

Preferably, letting $S_0$, t, and w be the area of the target measurement member requiring the fatigue damage diagnosis, the thickness of the target measurement member, and the width of the magnetic excitation head, respectively, the Barkhausen noise is measured in the region of the area S satisfying $0<S/S_0\leq 10^{-2}$ and located within the range of w or more to 200t or less from a reference position of the target measurement member, provided that the reference position is one of the welding and edge portion of the target measurement member.

A member of steelwork having a life diagnostic function comprises a system wherein a magnetic head constituted by a magnetic excitation head and a magnetic detection head is spaced apart above from a target measurement member requiring a fatigue damage diagnosis by a predetermined liftoff distance, the magnetic head has a function of AC-magnetizing a target measurement portion of the target measurement member with the magnetic excitation head and measuring Barkhausen noise with the magnetic detection head, and a degree of fatigue damage is diagnosed in accordance with one of a root-mean-square voltage and voltage amplitude value of the Barkhausen noise.

Preferably, the predetermined liftoff distance falls within the range of 5 $\mu$m or more to 4 mm or less. In addition, the Barkhausen noise is measured under the condition of 5 $\mu$m<d$\leq$1 where d is the detection depth of the Barkhausen noise in AC-magnetizing the target measurement portion with the magnetic head.

Preferably, letting $S_0$, t, and w be the area of the target measurement member requiring the fatigue damage diagnosis, the thickness of the target measurement member, and the width of the magnetic excitation head, respectively, the member of steelwork has a function of measuring the Barkhausen noise in the region of the area S satisfying 0<S/$S_0\leq 10^{-2}$ and located within the range of w or more to 200t or less from a reference position of the target measurement member, provided that the reference position is one of the welding and edge portion of the target measurement member.

Preferably, the target measurement member is a vibration-damping member having an external energy absorbing function by plastic deformation.

Preferably, the vibration-damping member is in the form of a wall.

Preferably, the vibration-damping member is in the form of a brace.

Preferably, the member of steelwork has a mechanism capable of measuring, during a use period, at least 70% of the region of the target measurement portion which is measured first with the magnetic head.

The present invention is a technique achieved by making extensive studies to seek for accurate diagnosis in view what means is available for diagnosing the degree of fatigue degradation by stress and strain in actual structural steelwork, and how to use the means. Steelwork is normally coated with a paint to prevent rust and improve the outer appearance. It is, therefore, impossible to bring a sensor or the like into direct contact with the surface of the target measurement object.

The present inventors has already invented a magnetic head capable of detecting Barkhausen noise in a noncontact manner (Japanese Patent Laid-Open No. 7-174730). The present inventors examined a method of easily and accurately diagnosing a target measurement object by using this magnetic head. The most important problem is a region of the member of steelwork to be measured. It is possible to predict stress acting on each member in the design stage and narrow a specific member to be measured down to some extent. References specifying a location to measure in the member are rarely available. The "member" is generally defined a steelwork unit whose two ends are fastened with welding or bolts in a construction site or the like. Cracking by fatigue is said to tend to generally occur from the uppermost surface of the steel material. It is very difficult to measure the Barkhausen noise on the uppermost surface because an oxide film or corrugations are present on the uppermost surface of an actual member of structural steelwork. According to studies of the present inventors, this surface state makes it difficult to bring the magnetic head into tight contact with the member of steelwork.

To stably apply the magnetic head to the target measurement surface with corrugations, the liftoff distance must be 5 $\mu$m or more. An increase in liftoff distance decreases the S/N ratio of the Barkhausen noise. The present inventors have found that a sufficient S/N ratio can be obtained within the liftoff distance range of 4 mm or less in tests of actual members of structural steelwork. Therefore, the liftoff distance of the magnetic head is defined to fall within the range of 5 $\mu$m or more to 4 mm or less.

The present inventors have examined the range of detection depth of the Barkhausen noise, by which the target fatigue degradation diagnosis can be performed with a sufficiently high accuracy. For this purpose, an AC current flows through the magnetic excitation head of the magnetic head having the above liftoff distance range to generate an AC magnetic field, for exciting the target measurement portion in this magnetic field. An AC voltage signal induced in the magnetic detection head in accordance with a change in magnetization of the target measurement portion is frequency-filtered to extract Barkhausen noise. Barkhausen noise is normally generated from the entire excited region of a ferromagnetic body such as steel upon excitation. According to the finding of the present inventors, when Barkhausen noise is measured under the condition of 5 $\mu$m$\leq$d$\leq$1 mm where d is the detection depth of the Barkhausen noise, the diagnostic accuracy is improved.

When the detection depth is smaller than 5 $\mu$m, dispersion of the Barkhausen noise due to the surface oxide layer or corrugations increases to degrade the diagnostic accuracy. When the detection depth is larger than 1 mm, the component of the Barkhausen noise which does not reflect fatigue degradation increases to degrade the diagnostic accuracy. Within the range of 40 $\mu$m$\leq$d$\leq$1 mm, the above influence of the surface layer portion can be further reduced to improve the diagnostic accuracy. By the above definitions, excitation need not be performed at a depth of 1 mm or more. This reduces the size of the magnetic excitation head. It is also found that a practically, sufficient diagnostic accuracy can be assured by using the RMS voltage or voltage amplitude value of the Barkhausen noise as a parameter representing the degree of fatigue and degradation.

As previous described, micro-cracking by fatigue is said to tend to occur from the surface of a member. In particular, fatigue degradation are said to tend to occur from a welding portion or a notch where stress concentrates. In the welding portion, a welding metal and a base material are different in magnetic permeability because their materials are different from each other. The flow of magnetic excitation fluxes is disturbed near the boundary of these materials, and uniform magnetic excitation cannot be performed accordingly. This decreases the detection sensitivity of the Barkhausen noise. The padding of the welding metal is present in the welding portion, or a plurality of plates are often welded at different angles. It is considerably difficult to apply the magnetic head direct to the welding portion itself and measure the Barkhausen noise. The edge portion of a member may be predicted to become a micro-cracking source by fatigue because notched corrugations tend to generate on the surface of the edge portion. As in the welding portion, the flow of magnetic excitation fluxes is disturbed at the edge portion because the base material and air are different in magnetic permeability. As a result, the detection sensitivity of the Barkhausen noise is lowered. It is also difficult to apply the magnetic head direct to the edge portion and measure the Barkhausen noise because the magnetic head cannot be stably applied to the edge portion. The edge portion indicates the edge portion of the member.

The present inventors have examined whether the degree of fatigue degradation in the edge or welding portion can be predicted and repair can be performed prior to destruction by not directly measuring the Barkhausen noise of the edge or welding portion but measuring the Barkhausen noise of a portion near the edge or welding portion. An increase in measurement area increases a probability capable of detecting micro-cracking by fatigue, thereby improving the diagnostic accuracy. Since this, however, is time-consuming and requires much labor, the measurement area must be minimized. The present inventors therefore examined a measurement area required for the diagnosis.

As described above, for example, it is possible to predict stress acting on each member constituting one steelwork in the design stage. A member requiring the diagnosis can be specified in the design stage. The area (surface area) of this member and its thickness are defined as $S_0$ and t, respectively. In this case, $S_0$ is the area of at least one surface of each plate material constituting the member, and t is its thickness. Normally, t is several mm to about 200 mm. A member identical to the actual member is used to perform a fatigue degradation simulation experiment in a laboratory to determine which surface portion on the member to be applied with the magnetic head and how to measure the surface portion.

The above experiment reveals the following findings. That is, assume that the reference position is the edge or welding portion of a member, and a magnetic head constituted by a magnetic detection head and a magnetic excitation head having a width w is used. In this case, when a region having the area S satisfying $0<S/S_0 \leq 10^{-2}$ in the region falling within the range of w or more to 200t or less from the reference position is measured, the degree of degradation of the region and hence the degree of degradation of the entire member can be diagnosed without directly measuring the edge or welding portion which is difficult to measure.

When a region to be measured is closer by w from the edge or welding portion, the flow of magnetic excitation fluxes is disturbed because the materials different in magnetic permeability are adjacent to each other, as described above. This disables uniform magnetic excitation, and reduces the detection sensibility of the Barkhausen noise. In addition, the manner to set the magnetic head becomes difficult. When the portion to be measured is separated from the edge or welding portion by 200t, the state of degradation of the edge or welding portion cannot be sensed. Therefore, the region to be measured is defined to fall within the range of w or more to 200t or less from the reference position.

The width w of the magnetic excitation head core is normally about several mm to about several cm. This width w is normally designed to be larger than the width of the magnetic detection head. When the portion having the area S is thick, measurement can be performed in a region extending in the direction of thickness. The minimum value of the area S is determined by the measurement area of the magnetic detection head constituting the magnetic head and generally about several mm². The diagnostic accuracy cannot be improved even with the area S satisfying $10^{-2}<S/S_0$, resulting in time-consuming and inefficient measurement with much labor. The area S is therefore defined to satisfy $0<S/S_0 \leq 10^{-2}$. To preferentially set efficiency, the diagnosis of fatigue degradation can be performed by measuring the region of the area S which satisfies $0<S/S_0 \leq 10^{-4}$ and is located within the range of w or more to 100t or less from the reference position. The area S may be the area of a single measurement portion or the total area of a plurality of measurement portions. In measuring the degree of degradation of the plurality of portions, the degree of degradation of the measurement member is preferably diagnosed using the measurement result of a portion in which fatigue degradation advances most.

In diagnosing the degree of fatigue degradation of a member of steelwork such as a bridge, a magnetic head can be easily applied to it even after construction, so that a diagnostic operation can be practiced, as needed. However, the members of steelwork in a building or the like cannot be easily applied with the magnetic head because most of the members are covered with the interior finish materials. Another feature of the present invention is a member of steelwork such as a steel frame or wall having a fatigue life self-diagnostic function, wherein a magnetic head is integrally fixed at a predetermined position of the member of steelwork.

That is, a member of steelwork comprises a system in which a magnetic head constituted by a magnetic excitation head and a magnetic detection head is disposed to be spaced apart above from a target measurement member requiring a fatigue damage diagnosis by a liftoff distance of 5 μm to 4 mm, the target measurement member is AC-magnetized with the magnetic excitation head, Barkhausen noise is detected with the magnetic detection head under a condition of 5 μm≦d<1 mm where d is a detection depth of the Barkhausen noise, and a degree of fatigue damage of a target measurement portion is diagnosed in accordance with one of a root-mean-square voltage and voltage amplitude value of the Barkhausen noise.

Letting $S_0$, t, and w be the area of the target measurement member requiring the fatigue damage diagnosis, the thickness of the target measurement member, and the width of the magnetic excitation head, respectively, the member of steelwork has a function of measuring the Barkhausen noise in the region of the area S satisfying $0<S/S_0 \leq 10^{-2}$ and located within the range of w or more to 200t or less from a reference position of the target measurement member, provided that the reference position is one of the welding and edge portion of the target measurement member, thereby assuring the practical accuracy. The reference position is defined as the edge or welding portion of the target measurement member.

Supply of an excitation current input to the magnetic excitation head and detection of a voltage signal induced by the magnetic detection head can be easily performed through a detachable input/output connector in the form of an outlet on a wall or the like. In addition, a radio unit can be used together with the magnetic head to transmit a voltage induced by the magnetic detection head in the form of a radio wave, thereby allowing centralized management. That is, the diagnosis can be performed continuously or every predetermined period. The member of steelwork having the life diagnostic function and integrally comprising the magnetic head must have a mechanism to fix the magnetic head, by which at least 70% of the region of the target measurement portion measured for the first time with the magnetic head can be measured during the use period. This is because the diagnostic accuracy of the target measurement portion is degraded when the magnetic head and the target measurement portion are shifted relative to each other during the use period and to allow the magnetic head measuring within smaller area smaller than 70% of the region.

The member of steelwork having the life diagnostic function can be used as the main-frame member of general structural steelwork to obtain its effect. This effect can be enhanced when the member of steelwork is applied as a vibration-damping member such as a damper designed such that the steelwork or steel wall itself absorbs the vibration energy (energy generated by an external force) generated by the wind and earthquake in a larger amount than any other member of steelwork. This is because the vibration-damping member is designed to be easily plastically deformed when an external force acts on it, so that the fatigue degradation concentrates on it. In this manner, the member of steelwork having the life diagnostic function is applied as a vibration-damping member or the like to allow the life diagnosis with high accuracy which cannot be obtained by the conventional techniques.

By using the method of diagnosing the fatigue life and the member of steelwork having the life diagnostic function according to the present invention, the wall and covering material need not be removed in practicing the fatigue life diagnosis for buildings and bridges. The degree of fatigue degradation by stress and strain in structural steelwork can be easily and accurately diagnosed prior to occurrence of cracking even in a location where an operator cannot access due to the structural limitation.

DETAILED DESCRIPTION OF THE PREFERRED EMBODIMENTS

Several preferred embodiments of the present invention will be described below with reference to the accompanying drawings.

First Embodiment

Figure 1:
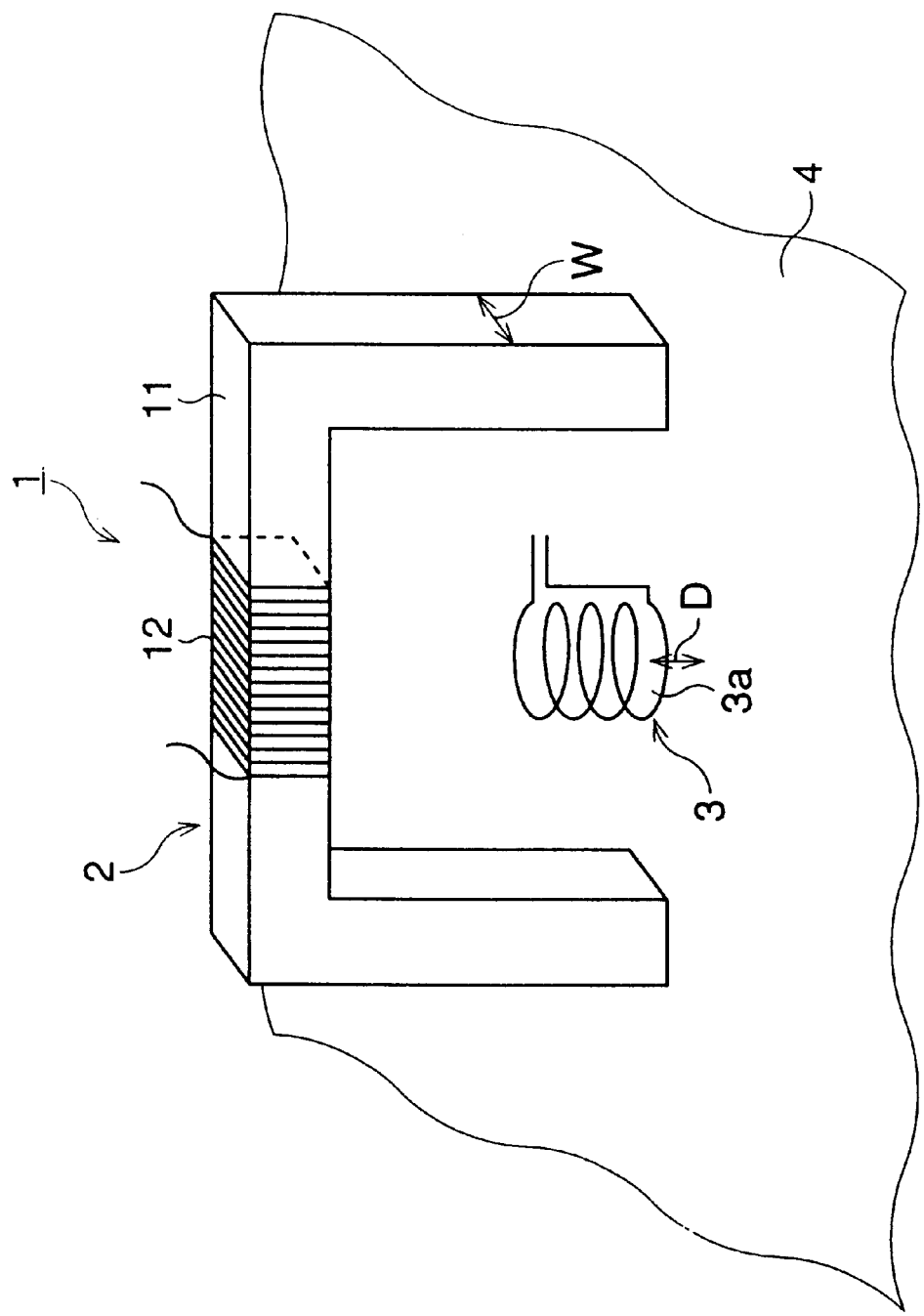
FIG. 1 is a schematic perspective view showing a structure of a magnetic head according to the first embodiment of the present invention.

The first embodiment will now be described below. The first embodiment exemplifies a method of diagnosing the fatigue life of a member of steelwork serving as a target measurement object by using a magnetic head. As shown in FIG. 1, a magnetic head 1 used in the first embodiment comprises a magnetic excitation head 2 and a magnetic detection head 3. The magnetic excitation head 2 has a U-shaped core 11 made of a soft magnetic material such as silicon steel sheet or an amorphous magnetic material and an excitation coil 12 obtained by winding a copper wire such as an enameled wire on the U-shaped core 11. The magnetic detection coil 3 comprises an air-core coil. In the magnetic head 1, the magnetic detection head 3 is disposed between the end portions of the U-shaped core 11 of the magnetic excitation head 2. A liftoff distance D between a lower end face 3a of the magnetic detection head 3 and the surface of a target measurement object 4 is set to fall within the range of 5 $\mu$m or more to 4 mm or less, and Barkhausen noise is measured.

A Barkhausen noise is practically measured using the magnetic head 1 at a detection depth d satisfying the condition of 5 $\mu$m $\leq d \leq 1$ mm. More specifically, the excitation frequency is set at a predetermined value so that the excitation depth is set to fall within the range of 5 $\mu$m or more to 1 mm or less. Alternatively, when an excitation region extends to a region deeper than 1 mm, the detection depth is set to fall within the range of 5 $\mu$m or more to 1 mm or less by setting the detection frequency to a predetermined value. In practice, one or both of the above settings can be used.

These techniques are based on the facts that an increase in excitation frequency decreases the depth of the excitation magnetic field and an increase in detection frequency allows detection of Barkhausen noise from a portion closer to the uppermost surface layer. In structural steelwork, the excitation frequency is set to several Hz to several hundred Hz, and the detection frequency is set to several ten Hz to about 10 MHz. When the Barkhausen noise is Fourier-transformed to obtain a frequency spectrum, the signal intensity generally decreases with an increase in frequency. To increase the S/N ratio, the maximum value of the detection frequency is preferably set to about 200 kHz.

Figure 2:
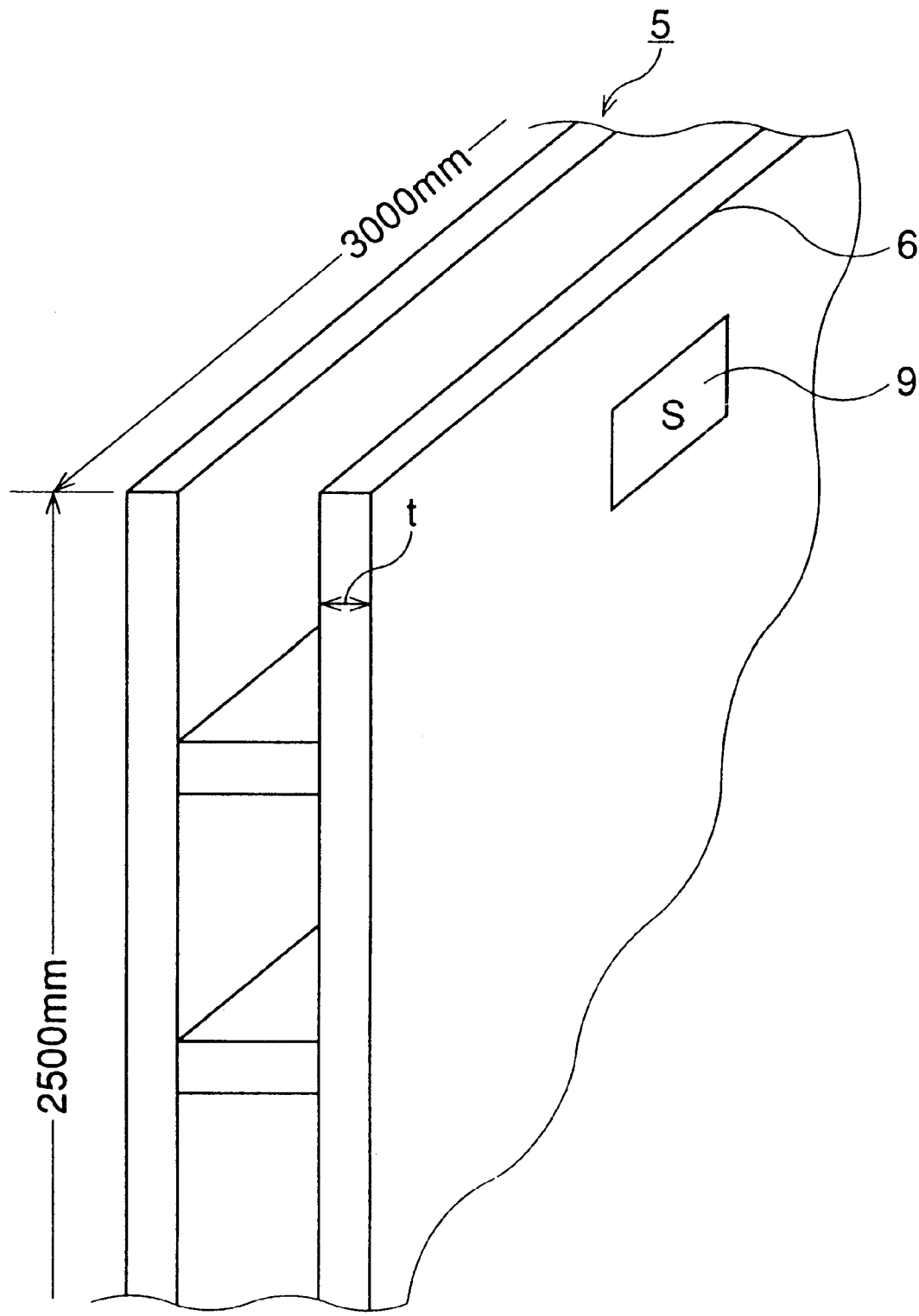
FIG. 2 is a schematic perspective view showing part of a structure (the reference position is an edge portion) to which the present invention is applied.
Figure 3:
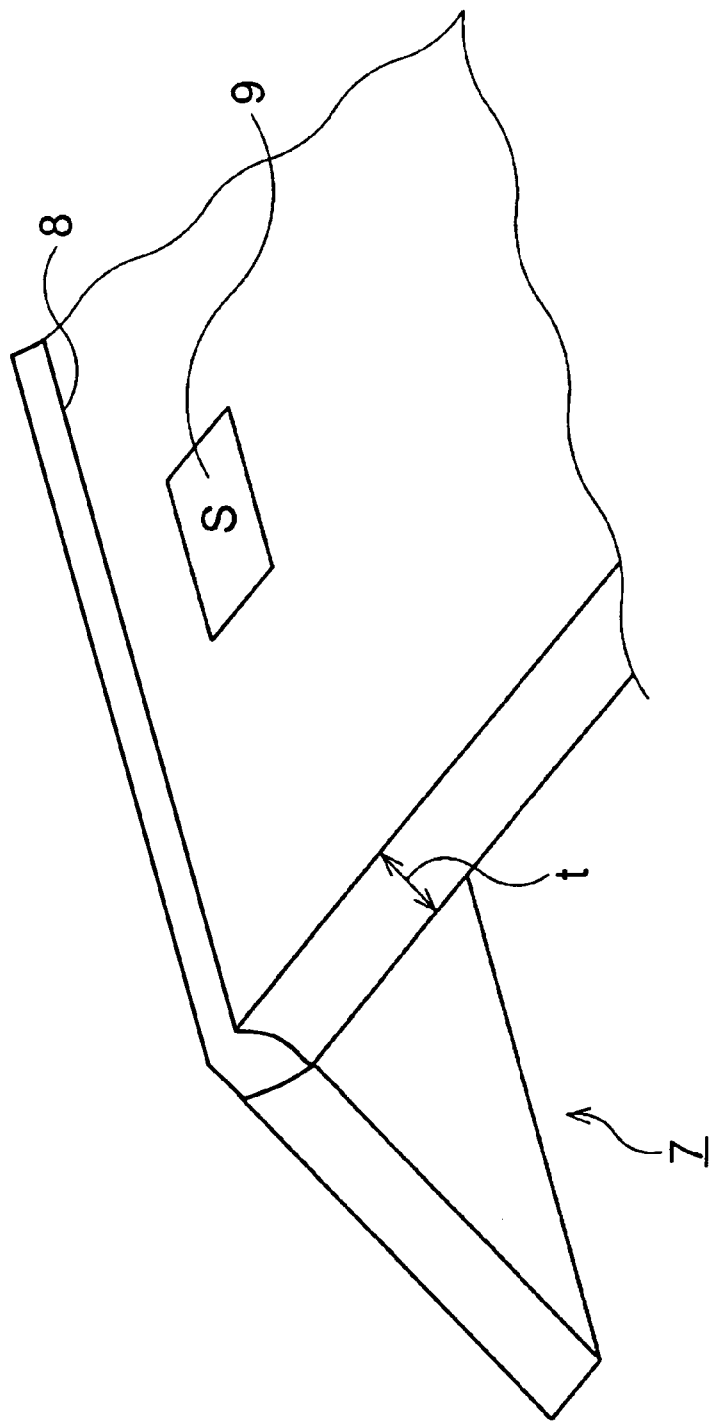
FIG. 3 is a schematic perspective view showing part of a structure (the reference position is a welding portion) to which the present invention is applied.

A region shown in FIG. 2 is diagnosed under the above conditions. FIG. 2 shows part of a member 5 of steelwork constituting structural steelwork such as a bridge or building. When the thickness of the member 5 of steelwork and the width of the magnetic excitation head 2 are represented by t and w, respectively, a region 9 of an area S satisfying $0 < S/S_0 \leq 10^{-2}$ and positioned in the range of w or more to 200t or less from an edge portion 6 serving as the reference position is measured. FIG. 3 is a schematic view showing a case using a member 7 of steelwork as a target measurement object and a welding portion 8 as the reference position.

The edge portion 6 or the welding portion 8 is selected as the reference position. if both portions exist in a member, both the portions are selected as the reference positions. If measurements are performed at a plurality of regions it improves diagnostic accuracy. If one of these portions must be selected, selection of the welding portion as the reference position allows the improvement of the diagnostic probability. If a portion on which stress or strain concentrates to advance fatigue degradation more than the edge portion 6 or the welding portion 8 is already known, this portion is selected as the reference position for better diagnostic accuracy.

According to the diagnostic method using the magnetic head 1 of the first embodiment, the degree of fatigue degradation by stress and strain in structural steelwork can be easily and accurately diagnosed prior to occurrence of cracking without any limitation on diagnostic locations.

Second Embodiment

The second embodiment will be described below. The second embodiment exemplifies a member of steelwork having a magnetic head 1 for diagnosing the fatigue life of a target measurement object. The same reference numerals as in the first embodiment denote the same members corresponding to the magnetic head 1 and the like described with reference to the first embodiment, and a detailed description thereof will be omitted.

Figure 4:
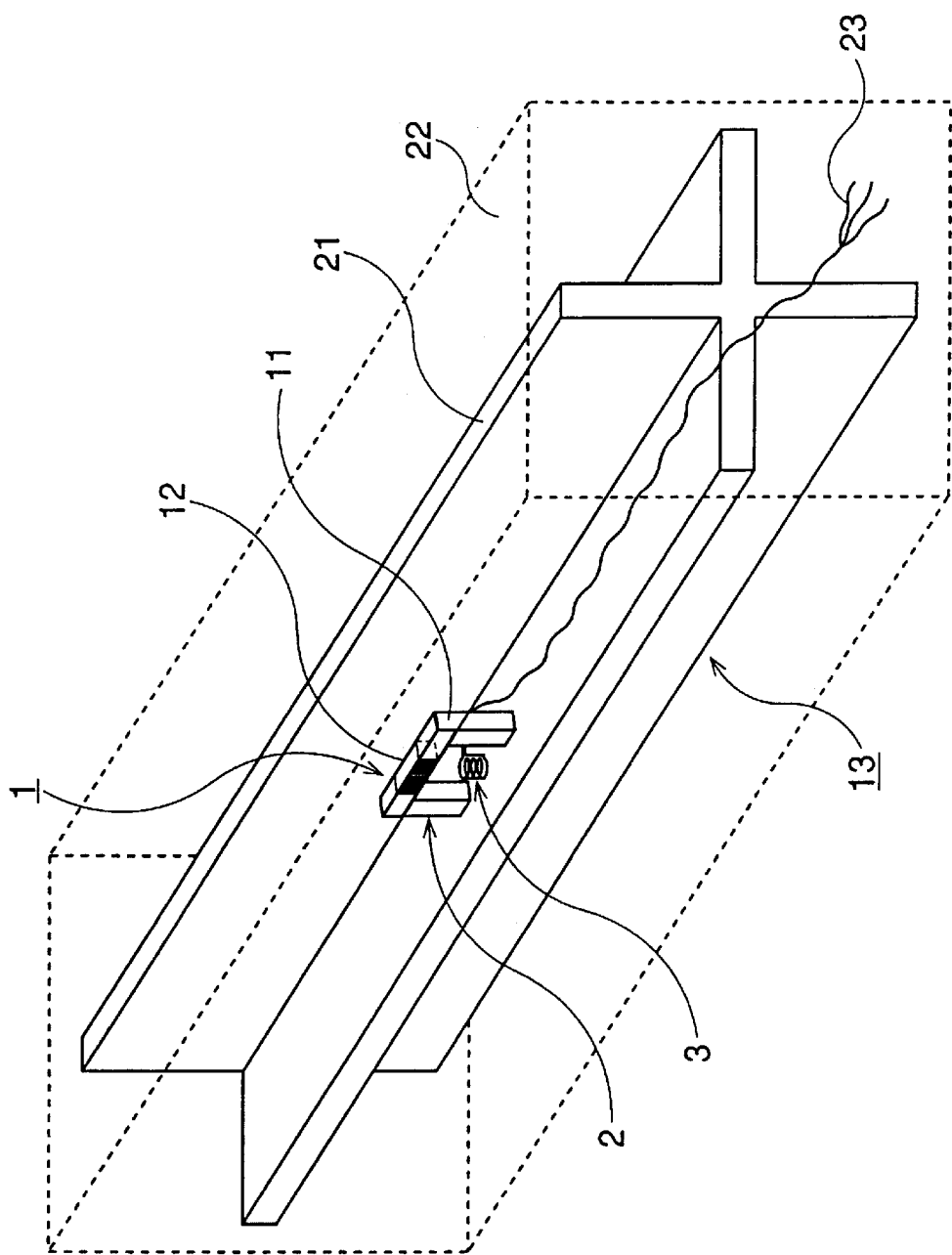
FIG. 4 is a schematic perspective view showing a structure of a member of steelwork having a life diagnostic function according to the second embodiment of the present invention.

As shown in FIG. 4, a member 13 of steelwork having a life diagnostic function is a so-called brace-like vibration-damping member and comprises a plate 21 of very low-yield steel and a magnetic head 1 identical to that of the first embodiment and formed on the surface of the plate 21. The plate 21 and the magnetic head 1 are embedded in mortar 22 indicated by a broken line in FIG. 4. The magnetic head 1 is fixed to be spaced apart from the surface of the plate 21 by the above-mentioned liftoff distance D. Wiring 23 connected to the magnetic head 1 are led out from the mortar 22.

Figure 5:
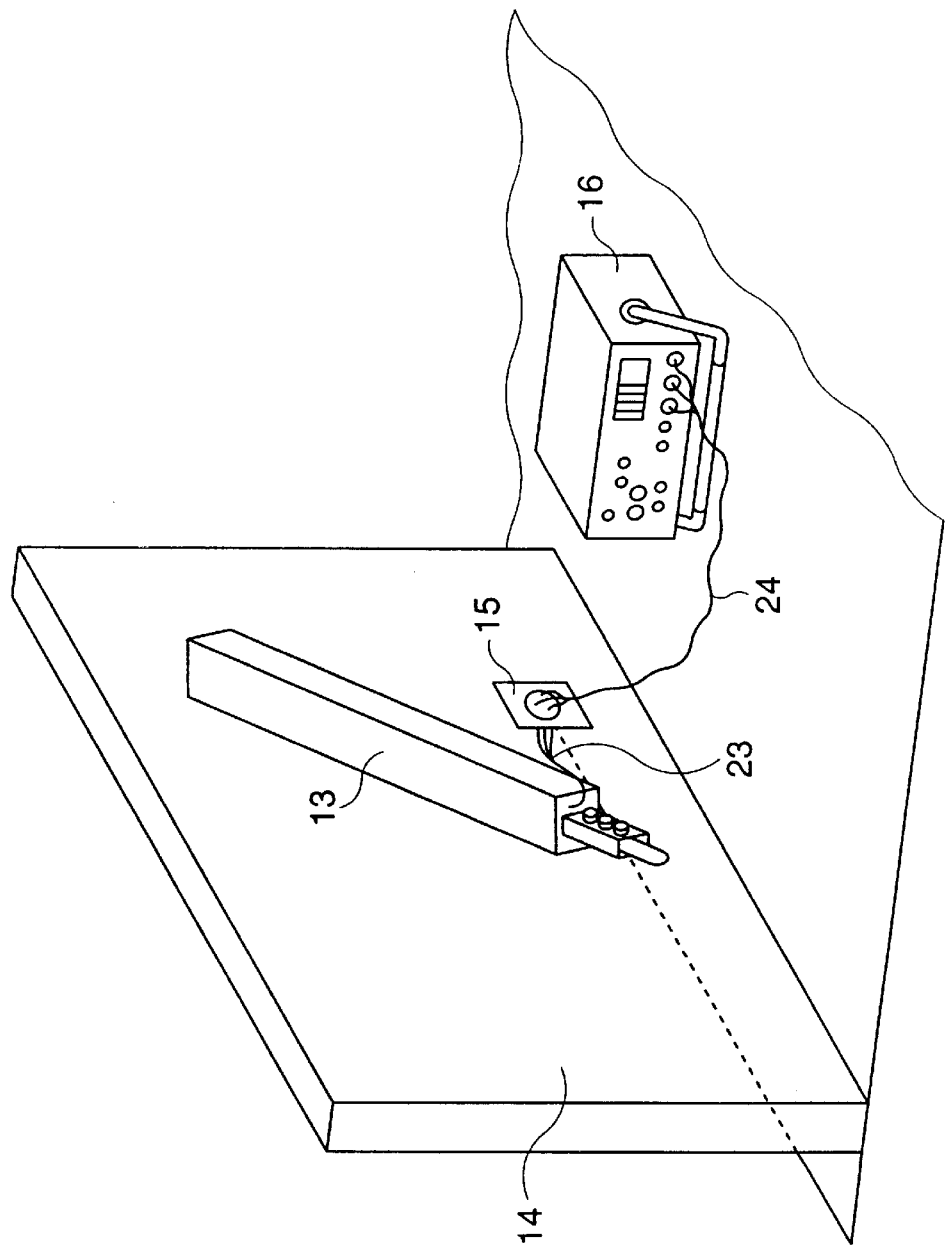
FIG. 5 is a schematic perspective view showing the layout of the member of steelwork having the life diagnostic function according to the second embodiment of the present invention.

FIG. 5 is a schematic view showing the layout in which the member 13 of steelwork is mounted on a wall 14. In this case, wiring 23 is connected to a connector 15 in the form of an AC outlet mounted on the wall 14. A cord 24 of a Barkhausen noise analyzing unit 16 having a predetermined excitation current supply function and a detected voltage signal analyzing function is plugged into the connector 15 to allow supply of the excitation current to the magnetic head 1 and at the same time detection of Barkhausen noise.

Figure 6:
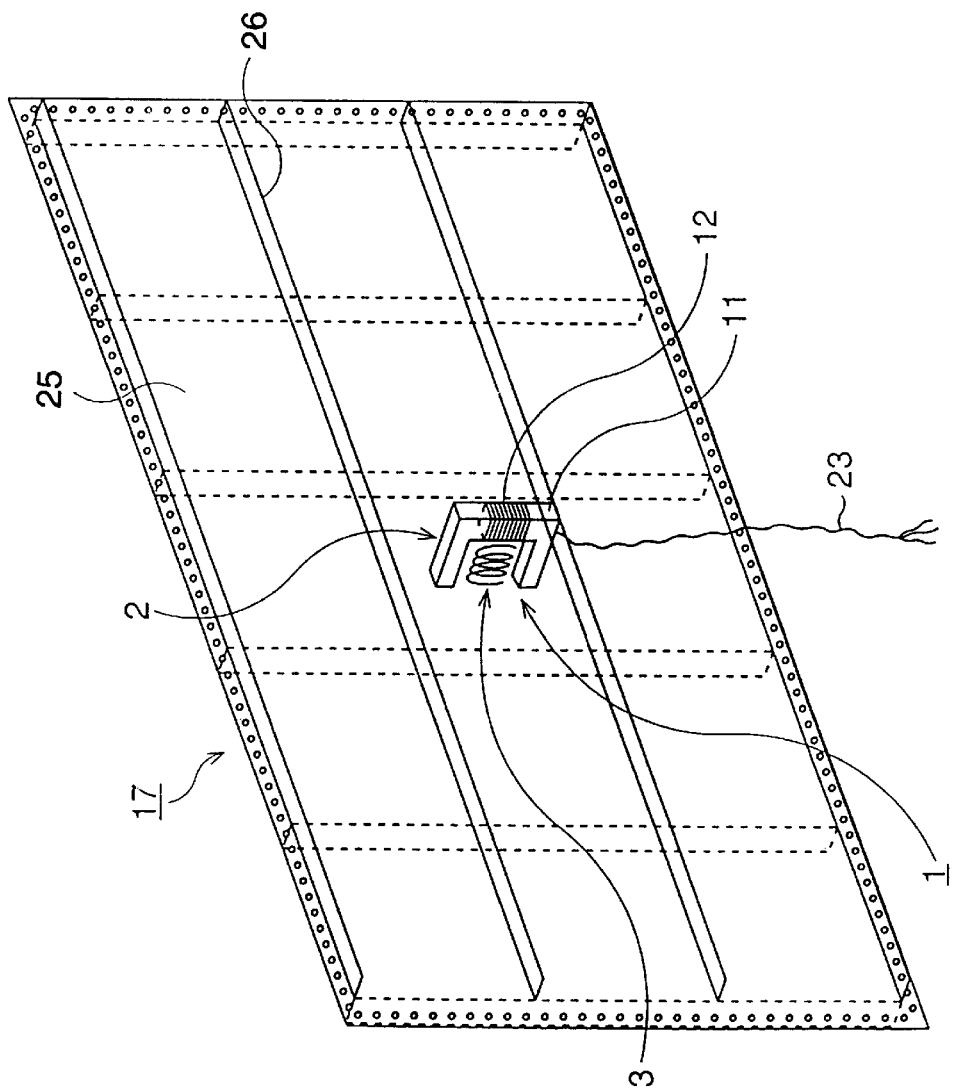
FIG. 6 is a schematic perspective view showing another structure of the member of steelwork having the life diagnostic function according to the second embodiment of the present invention.

FIG. 6 shows another structure of the member of steelwork having the life diagnostic function. A member 17 of steelwork is a wall-like vibration-damping member and comprises a plate 25 of very low-yield steel, a magnetic head 1 identical to that of the first embodiment and mounted on the surface of the plate 25, and a grid-like skeltal member 26 of steelwork fixed to the surface of the plate 25. The member 17 is thus constituted by the plate 25, the magnetic head 1, and the skeltal member 26. In this case, the magnetic head 1 is fixed to be spaced apart from the surface of the plate 25 by the above-mentioned liftoff distance D.

By using the members 13 and 17 of steelwork having the life diagnostic function according to the second embodiment, the wall or covering material need not be removed even in fatigue life diagnoses of buildings, bridges, and the like. In addition, the degree of fatigue degradation by stress and strain in structural steelwork can be easily and accurately diagnosed prior to occurrence of cracking even in a location where an operator cannot access.

The present invention will be described in detail by way of its examples.

Experimental Example 1

Changes in Barkhausen noise upon repeatedly loading a tensile stress and compression stress axially parallel to test pieces (sectional dimensions: 8 mm×8 mm; length: 50 mm) of very-low-yield steel (yield point=about 10 kg/mm$^2$) were examined as a function of stress load repetition count. The loaded stresses in equivalent strain values were ±0.05% and ±0.5%. The excitation and detection frequencies as the Barkhausen noise detection conditions were 100 Hz and 10 kHz to 100 kHz, respectively. The liftoff distance between the detection head and the target measurement portion surface was about 1 mm. The Barkhausen noise detection depth d under these conditions was about 200 μm.

Figure 7:
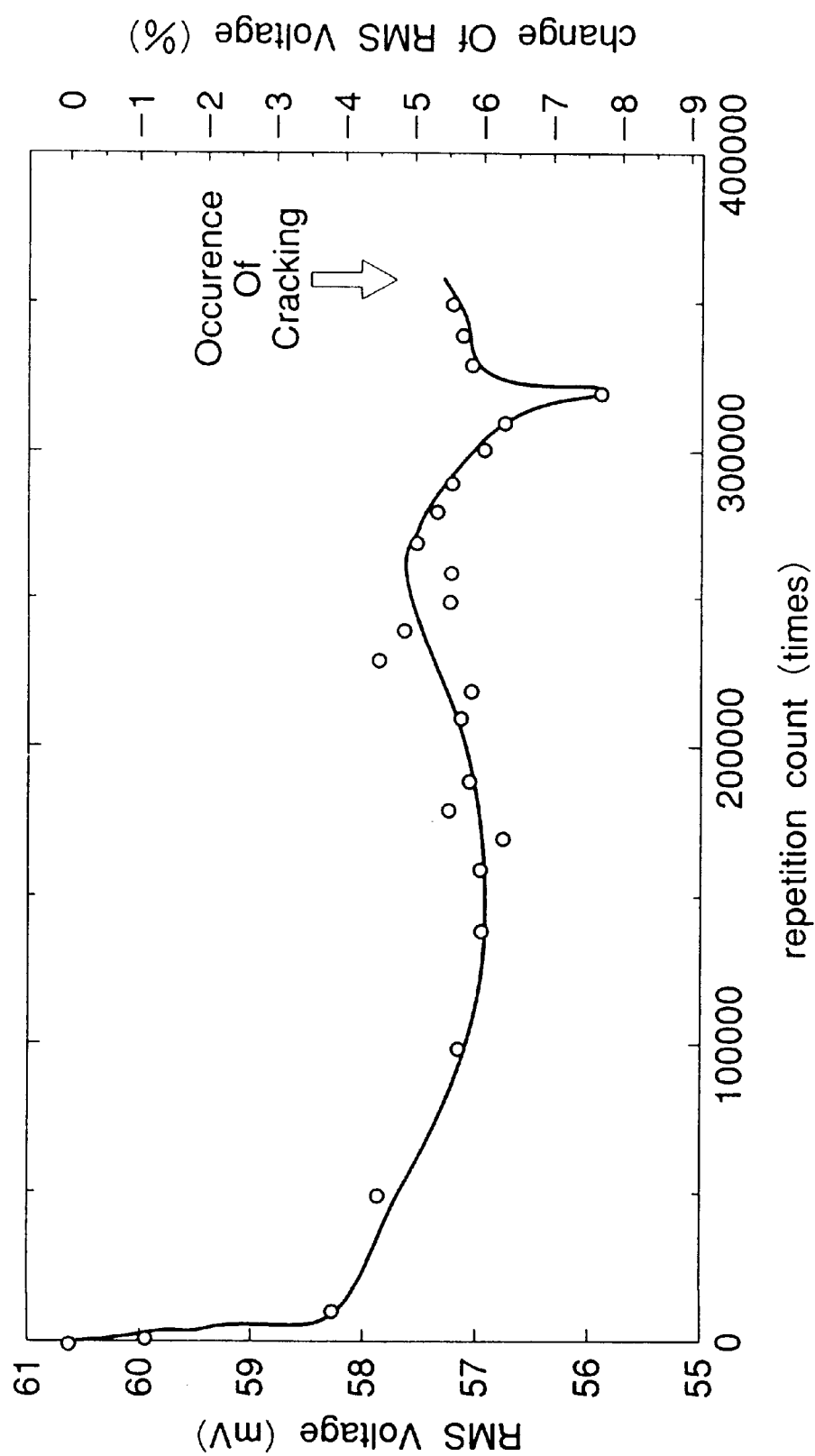
FIG. 7 is a graph showing a change in Barkhausen noise as a function of the repetition count in a fatigue test (strain: ±0.05%)
Figure 8:
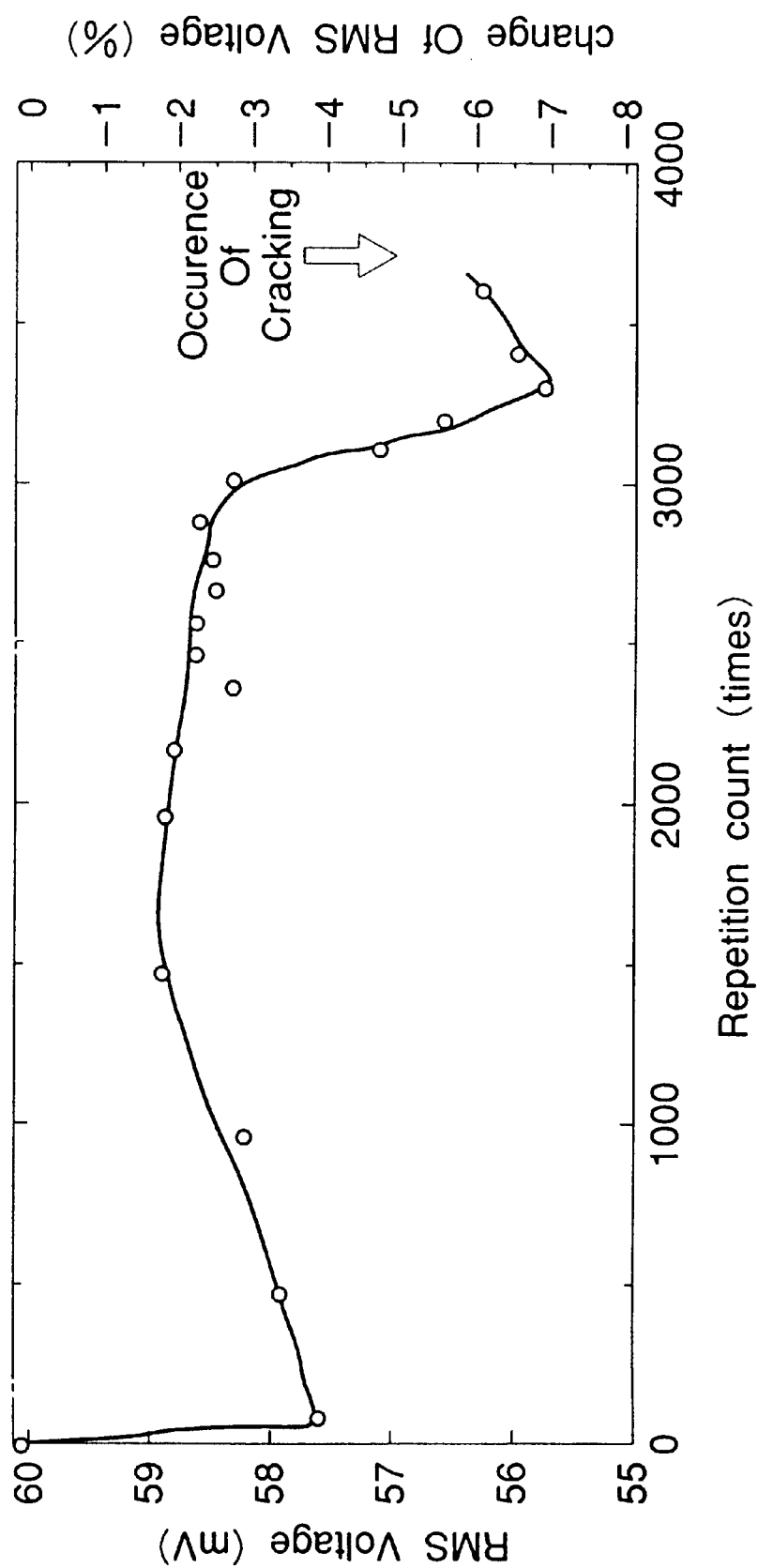
FIG. 8 is a graph showing a change in Barkhausen noise as a function of the repetition count in a fatigue test (strain: ±0.5%)

The results of Barkhausen noise figured using RMS voltages are shown in FIG. 7 (strain: ±0.05%) and FIG. 8 (strain: ±0.5%). In both the cases in FIGS. 7 and 8, the RMS voltages abruptly decrease before cracking occurs, and then abruptly increase. By detecting the abrupt changes in these RMS voltages, fatigue lives prior to occurrence of cracking can be accurately diagnosed.

Voltage amplitudes change in the similar manners as in FIGS. 7 and 8 in the results of detection of Barkhausen noise voltage amplitude values as a function of the stress load repetition count. It appeared that the fatigue lives can be diagnosed prior to occurrence of cracking by detecting these changes.

Experimental Example 2

A shear strain of ±1% was longitudinally loaded on test members (thickness of member: 5 mm, length: 3,000 mm, width: 2,500 mm) of rolled steel sheet SM400 for welding structure shown in FIG. 2 by using a large test machine to examine on the basis of the load repetition count and the changes in Barkhausen noise whether the fatigue life could be diagnosed. As shown in FIGS. 7 and 8, when an abrupt change in Barkhausen noise can be sensed prior to occurrence of cracking, the determination is made as "diagnosable"; otherwise, "undiagnozable".

In this experiment, the detection depth of the Barkhausen noise was variously changed to check. A magnetic head 1 having the magnetic excitation head width of 10 mm and the magnetic detection head measurement area of 20 mm$^2$ was used. The liftoff distance D of the magnetic head 1 was 0.6 mm. The excitation frequency was changed within the range of 2 Hz to 100 Hz and the detection frequency was changed within the range of 10 Hz to 20 MHz to change the detection depth d of the Barkhausen noise. Permeation depth of the excitation magnetic field from the surface and reacheability distance of the noise source when the Barkhausen noise source was located inside in the direction of depth, were evaluated using Skin Depth=$(\rho/\pi f\mu)^{1/2}$ (where f: frequency, $\mu$: magnetic permeability, $\rho$: resistivity). That is, the detection depth d of the Barkhausen noise was evaluated using this Skin Depth. Each experiment was conducted 10 times under the same condition, and each sample piece was evaluated by a count by which occurrence of cracking could be predicted. The relationship between the detection depth d and the diagnostic accuracy is shown in Table 1.

TABLE 1

| Detection Depth (mm) | Diagnostic Probability (%) |
| --- | --- |
| 0.003(3μm) | 60 |
| 0.006 | 80 |
| 0.02 | 80 |
| 0.04 | 90 |
| 0.08 | 90 |
| 0.1 | 90 |
| 0.3 | 100 |
| 0.5 | 100 |
| 0.7 | 90 |
| 1.0 | 80 |
| 1.2 | 70 |
| 1.5 | 70 |
| 2.0 | 70 |

As can be apparent from Table 1, the fatigue life can be diagnosed with a high accuracy of 80% or more at the detection depth d of 5 μm or more to 1 mm or less. In addition, when the detection depth d is set to fall within the range of 40 μm or more to 0.7 mm or less, the fatigue life can be diagnosed with a higher accuracy of 90% or more.

Experimental Example 3

An arbitrary position was selected in a member of structural steelwork shown in FIG. 2, a liftoff distance D of a magnetic head 1 was changed at each position, and the Barkhausen noise was measured 10 times at each liftoff distance D. The magnetic head 1 was identical to that in Experimental Example 2. The excitation and detection frequencies were set to 100 Hz and 10 kHz to 100 kHz, respectively. The detection depth d of the Barkhausen noise was about 200 $\mu$m. The maximum, minimum, and average values of the RMS voltages of Barkhausen noise measured 10 times are shown in Table 2.

TABLE 2

| Liftoff Distance (mm) | RMS Voltage (mV) | | | |
|---|---|---|---|---|
| | Maximum Value | Minimum Value | Average Value | Maximum value − Minimum value |
| 0 | 44.3 | 41.6 | 43 | 2.7 |
| 0.003 | 42.7 | 39.9 | 42 | 2.8 |
| 0.007 | 42.6 | 41.3 | 42 | 1.3 |
| 0.08 | 38.7 | 37.5 | 38 | 1.2 |
| 0.8 | 33.3 | 32.5 | 33 | 0.8 |
| 1.0 | 31.4 | 30.7 | 31 | 0.7 |
| 2.0 | 25.3 | 24.7 | 25 | 0.6 |
| 3.0 | 22.5 | 21.8 | 22 | 0.7 |
| 3.5 | 20.3 | 19.5 | 20 | 0.8 |
| 4.5 | 18.4 | 17.7 | 18 (decrease in S/N) | 0.7 |
| 5.0 | 17.3 | 16.5 | 17 (decrease in S/N) | 0.8 |

Judging from the above results, when the liftoff distance D is smaller than 5 $\mu$m (0.005 mm), the magnetic head 1 applied to the target measurement surface becomes unstable due to the corrugations of the target measurement surface, and the difference between the maximum and minimum values becomes large. When a diagnosis is performed by one measurement result, the diagnostic accuracy is reduced. When the liftoff distance D exceeds 4 mm, the RMS voltage lowers to decrease the S/N ratio, thereby degrading the diagnostic accuracy. Therefore, the diagnostic accuracy is improved when the liftoff distance D is set to 5 $\mu$m or more to 4 mm or less.

Experimental Example 4

Using a member identical to that of Experimental Example 2, a test for loading a repeated strain was conducted, and it was determined on the basis of the load repetition count and the changes in Barkhausen noise whether the fatigue life was diagnosed. A method of determining whether a diagnosis can be performed is identical to that of Experimental Example 2. In this experiment, examinations were made when the position of a measurement portion and its measurement area were variously changed using the edge portion as the reference position. The excitation and detection frequencies were the same as those of Experimental Example 3. The liftoff distance D was set to 0.6 mm. The width w of the magnetic excitation head was 10 mm, and the area which could be measured each time when the magnetic head 1 applied to the target measurement object was 20 mm². A total area $S_0$ of the member used this time was 15×10⁶ mm² (the area on one surface of one steel sheet was 7.5×10⁶ mm²). This experiment was performed 10 times on each condition, and the evaluation was made on the basis of a count which could predict occurrence of cracking. The results are summarized in Tables 3 and 4.

TABLE 3

| Distance of Measurement Portion from Reference Position | Diagnostic Probability (%) |
|---|---|
| 0.5w | 60 |
| w(= 10 mm) | 90 |
| 40t | 90 |
| 60t | 100 |
| 80t | 100 |
| 100t | 100 |
| 140t | 80 |
| 180t | 80 |
| 200t | 80 |
| 240t | 70 |

TABLE 4

| S/So | Diagnostic Probability (%) |
|---|---|
| $10^{-6}$ | 80 |
| $10^{-5}$ | 80 |
| $10^{-4}$ | 90 |
| $10^{-3}$ | 100 |
| $10^{-2}$ | 100 |
| $10^{-1}$ | 100 |
| $3 \times 10^{-1}$ | 100 |

In Table 3, the detection sensitivity of Barkhausen noise at a portion closer than w was reduced, and the way of bringing the magnetic head 1 to the target measurement surface varied to degrade diagnostic accuracy. At a portion separated from the 200t position, the influence from the reference position was reduced to degrade the diagnostic accuracy. When the diagnostic portion was set at a position of 200t or less from the reference position, the degree of fatigue and degradation can be diagnosed with a probability of 80% or more. In addition, when the diagnostic portion is set at a position of w or more to 100t or less from the reference position, the degree of fatigue and degradation can be diagnosed with a probability of 90% or more.

As can be apparent from Table 4, the diagnosis can be performed with an accuracy of 80% or more in the entire $S/S_0$ range. Even if the ratio $S/S_0$ is set higher than $10^{-2}$, a further improvement in accuracy cannot be made, and only the working efficiency is decreased. When the measurement area S is set to satisfy $0<S/S_0 \leq 10^{-2}$ to assure a practical measurement efficiency and allow the fatigue degradation diagnosis with a high probability of 80% or more. In particular, the diagnosis can be performed with a probability of almost 90% or more for $10^{-4} \leq S/S_0 10^{-2}$. To preferentially improve efficiency, the condition is set to $0 \leq S/S_0 \leq 10^{-4}$ which allows the fatigue degradation diagnosis with a probability of 80 to 90%.

Judging from the above results, the Barkhausen noise in the region of the area S satisfying $0 \leq S/S_0 \leq 100^{-2}$ and located within the range of w or more to 200t or less is measured using the edge portion of the target measurement member as the reference position, thereby diagnosing the fatigue life of structural steelwork.

A similar experiment was conducted using a welding portion as the reference position in a member of steelwork having the welding portion, and the results similar to Tables 3 and 4 are obtained. It was thus found that the fatigue life of the structural steelwork could be diagnosed by measuring the Barkhausen noise in the region of the area S satisfying $0 \leq S/S_0 \leq 10^{-2}$ and located within the range of w or more to 200t or less.

Experimental Example 5

Figure 9:
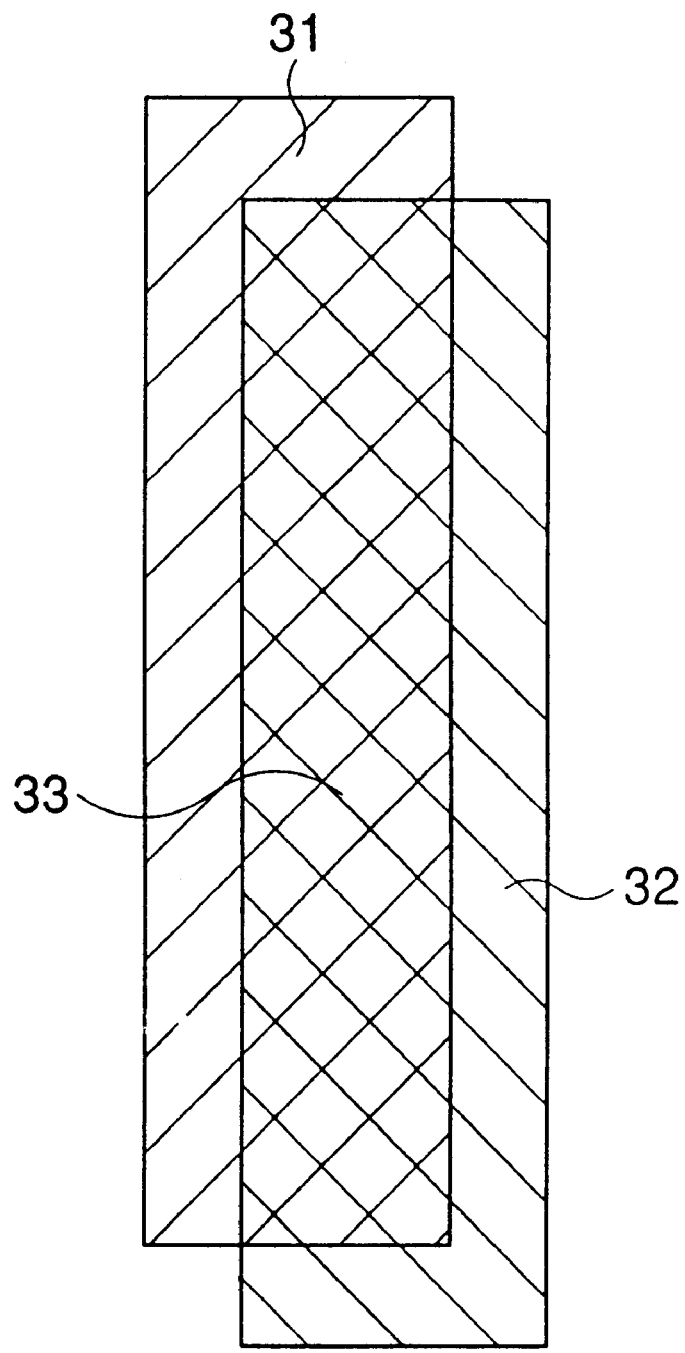
FIG. 9 is a view showing a region detected by a magnetic detection coil before and after the fatigue test.

A fatigue simulation experiment assuming the earthquake vibrations was conducted for steelwork using a member 13 of steelwork having a life diagnostic function in which a magnetic head 1 was fixed to a plate 21 of a brace type shown in FIG. 4 until visual cracking occurred. At this time, the fixing method of the magnetic head 1 was variously changed to evaluate the diagnostic accuracy. Steelwork was made of very-low-yield steel as in Experimental Example 1, which had a length of 2,000 mm, a width of 200 mm, and a thickness of 15 mm. The fixing method of the magnetic head 1 was changed to shift the magnetic head 1 during the test. The magnetic head 1 was disposed near the center of the plate 21 at the 3t position from the edge portion before the test. The liftoff distance D was 0.6 mm. As shown in FIG. 9, when the area of regions 31 and 32 (the region 31 is position before the test, and the region 32 is a a region at the position after the test) measured by a magnetic detection head 3 is defined A, and the area of an overlapping region 33 before and after the shift is defined as B. In this case, the shift amount of the magnetic head 1 is defined as (B/A)×100 (%). measurement area of the magnetic detection head 3 is 20 mm². As shown in FIG. 7 or 8, the evaluation of the diagnostic accuracy is performed by determining whether an abrupt change in Barkhausen nose can be detected prior to occurrence of cracking. If possible, determination is made as "diagnozable"; otherwise, "undiagnozable". The abrupt change in the current experiment was a decrease in RMS voltage of the Barkhausen noise by 3% or more prior to occurrence of cracking.

The experiment results are shown in Table 5.

TABLE 5

| (B/A) × 100% | Rate of Decrease in RMS Voltage (%) | Determination |
| --- | --- | --- |
| 100 | 6.2 | diagnozable |
| 92 | 5.8 | diagnozable |
| 83 | 4.1 | diagnozable |
| 72 | 3.5 | diagnozable |
| 58 | 2.3 | undiagnozable |
| 42 | increase by 4% | undiagnozable |

(B/A)×100 (%) as the shift amount of the magnetic head 1 is a parameter representing how many percentage of the region of the portion measured first is measured during the use period. When the percentage is 70% or more, an abrupt decrease in RMS voltage is 3% or more so that the diagnosis becomes possible. If the percentage is 42%, the RMS voltage is increased. This is, however, because the RMS voltage at a newly measured portion is high due to the shift of the magnetic detection head. In this case, a continuous curve shown in FIG. 7 or 8 cannot be plotted, and the fatigue life cannot be diagnosed.

Judging from the above description, if the shift of the measurement area from the first fixed position falls within the range of at most 30%, i.e., if at least 70% of the region of the target measurement portion measured first is possible even upon occurrence of the shift in measurement area, a sufficient diagnostic accuracy can be obtained.

What is claimed is:

1. A member of steelwork having a life diagnostic function, comprising a system wherein
   a magnetic head constituted by a magnetic excitation head and a magnetic detection head is spaced apart above from a target measurement member requiring a fatigue damage diagnosis by a predetermined liftoff distance,
   the magnetic head has a function of AC-magnetizing a target measurement portion of the target measurement member with the magnetic excitation head and measuring Barkhausen noise with the magnetic detection head, and
   a degree of fatigue damage is diagnosed in accordance with one of a root-mean-square voltage and voltage amplitude value of the Barkhausen noise.

2. A member according to claim 1, wherein the target measurement member is a vibration-damping member having an external energy absorbing function by plastic deformation.

3. A member according to claim 1, wherein the member of steelwork has a mechanism capable of measuring, during a use period, at least 70% of the region of the target measurement portion which is measured first with the magnetic head.

4. A member according to claim 1, wherein the predetermined liftoff distance falls within a range of not less than 5 $\mu$m to not more than 4 mm, and
   the Barkhausen noise is measured under a condition of 5 $\mu$m $\leq$ d $\leq$ 1 mm where d is the detection depth of the Barkhausen noise in AC-magnetizing the target measurement portion with the magnetic head.

5. A member according to claim 1, wherein letting $S_0$, t, and w be the area of the target measurement member requiring the fatigue damage diagnosis, the thickness of the target measurement member, and the width of the magnetic excitation head, respectively, the member of steelwork has a function of measuring the Barkhausen noise in a region of an area S satisfying $0<S/S_0 \leq 10^{-2}$ and located within a range of not less than w to not more than 200t from a reference position of the target measurement member, provided that the reference position is one of a welding and edge portion of the target measurement member.

6. A member according to claim 5, wherein the target measurement member is a vibration-damping member having an external energy absorbing function by plastic deformation.

7. A member according to claim 6, wherein the vibration-damping member is in the form of a wall.

8. A member according to claim 6, wherein the vibration-damping member is in the form of a brace.

9. A member according to claim 7, wherein the member of steelwork has a mechanism capable of measuring, during a use period, at least 70% of the region of the target measurement portion which is measured first with the magnetic head.

10. A member according to claim 8, wherein the member of steelwork has a mechanism capable of measuring, during a use period, at least 70% of the region of the target measurement portion which is measured first with the magnetic head.

11. A member according to claim 4, wherein letting $S_0$, t, and w be the area of the target measurement member requiring the fatigue damage diagnosis, the thickness of the target measurement member, and the width of the magnetic excitation head, respectively, the member of steelwork has a function of measuring the Barkhausen noise in a region of an area S satisfying $0<S/S_0 \leq 10^{-2}$ and located within a range of not less than w to not more than 200t from a reference position of the target measurement member, provided that the reference position is one of a welding and edge portion of the target measurement member.

12. A member according to claim 11, wherein the target measurement member is a vibration-damping member having an external energy absorbing function by plastic deformation.

13. A member according to claim 2, wherein the vibration-damping member is in the form of a wall.

14. A member according to claim 2, wherein the vibration-damping member is in the form of a brace.

15. A member according to claim 12, wherein the vibration-damping member is in the form of a wall.

16. A member according to claim 12, wherein the vibration-damping member is in the form of a brace.

17. A member according to claim 13, wherein the member of steelwork has a mechanism capable of measuring, during a use period, at least 70% of the region of the target measurement portion which is measured first with the magnetic head.

18. A member according to claim 14, wherein the member of steelwork has a mechanism capable of measuring, during a use period, at least 70% of the region of the target measurement portion which is measured first with the magnetic head.

19. A member according to claim 15, wherein the member of steelwork has a mechanism capable of measuring, during a use period, at least 70% of the region of the target measurement portion which is measured first with the magnetic head.

20. A member according to claim 16, wherein the member of steelwork has a mechanism capable of measuring, during a use period, at least 70% of the region of the target measurement portion which is measured first with the magnetic head.

* * * * *